United States Patent [19]
LaRosa et al.

[11] Patent Number: 5,326,564
[45] Date of Patent: Jul. 5, 1994

[54] RESEALABLE COSMETIC PRODUCT

[75] Inventors: Joseph LaRosa, Danbury; John Vaccaro, Stamford, both of Conn.; Victoria Connell, New York, N.Y.

[73] Assignee: Elizabeth Arden Co., Division of Conopco, Inc., New York, N.Y.

[21] Appl. No.: 981,708

[22] Filed: Nov. 25, 1992

[51] Int. Cl.⁵ .................. A45D 40/00; A61K 9/48
[52] U.S. Cl. ............................ 424/401; 215/6; 220/DIG. 26; 424/451; 424/59; 424/684; 514/881; 514/275
[58] Field of Search ............ 424/451, 454, 401; 215/6; 220/DIG. 26

[56] References Cited

U.S. PATENT DOCUMENTS

| D. 58,075 | 6/1921 | Davis | D0/327 |
|---|---|---|---|
| D. 269,718 | 7/1983 | Tovey | D28/2 |
| D. 327,216 | 6/1992 | Connell | D9/302 |
| 582,021 | 5/1987 | Morstadt | 424/451 |
| 1,888,314 | 11/1932 | Framke | 206/229 |
| 2,562,402 | 7/1951 | Winsten | 167/63 |
| 2,580,414 | 1/1952 | Duffey | 206/84 |
| 2,717,473 | 9/1955 | Moore | 46/178 |
| 4,132,306 | 1/1979 | Margolin | 206/37 |
| 4,685,558 | 8/1987 | Filiz | 206/1.5 |
| 4,815,608 | 3/1989 | Silberberg | 132/295 |
| 5,009,341 | 4/1991 | Broxton | 222/130 |
| 5,064,082 | 11/1991 | Lombardi et al. | 215/6 |

FOREIGN PATENT DOCUMENTS 1420234 1/1976 United Kingdom .

Primary Examiner—Thurman K. Page
Assistant Examiner—Sally Gardner
Attorney, Agent, or Firm—Milton L. Honig

[57] ABSTRACT

A cosmetic product is provided that includes a cosmetic composition and a container for storing same. The container has a first and second section. Each section is defined by a hemispheroidal chamber having an open mouth with a circumferential edge therearound and a flange projecting outwardly therefrom. The first section contains the cosmetic composition and is sealed by a web completely covering the mouth as well as the flange. On the flange of the second section is a lip with a clamping device for releasably engaging the first section flange thereby releasably joining first and second sections to one another.

16 Claims, 1 Drawing Sheet

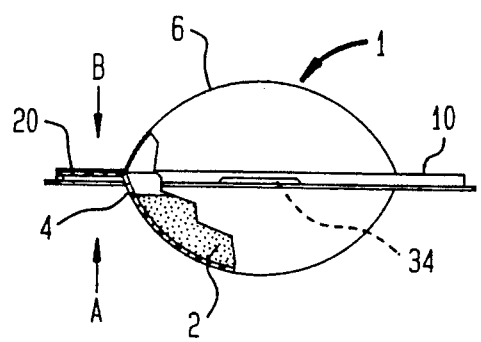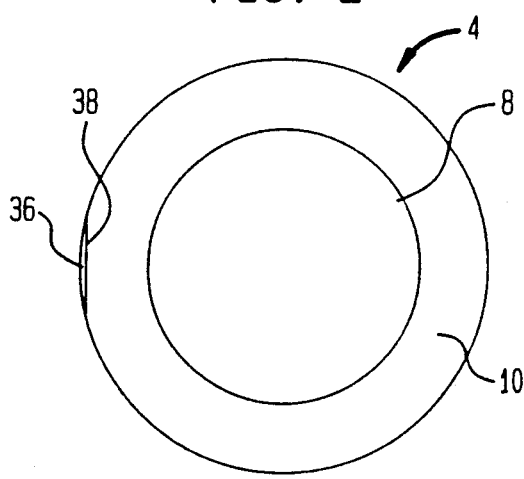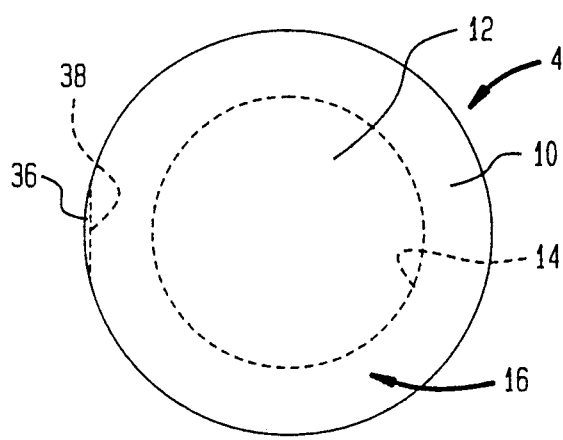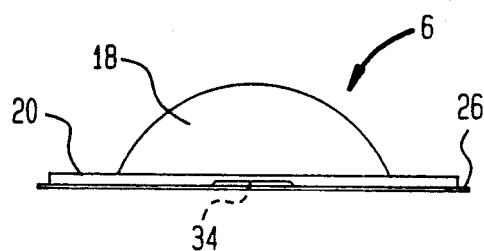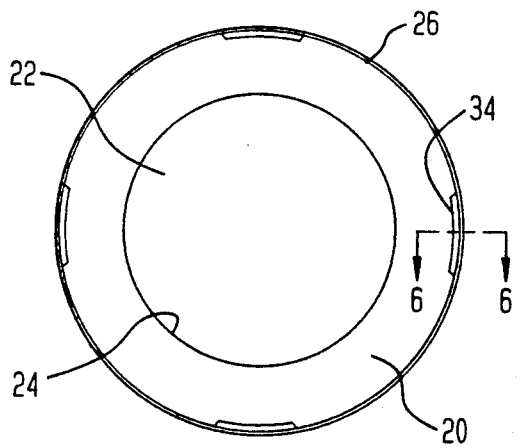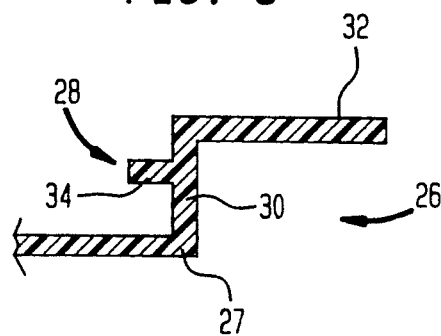

5,326,564

RESEALABLE COSMETIC PRODUCT

BACKGROUND OF THE INVENTION

1. Field of the Invention

The invention relates to a resealable sampling capsule or container for cosmetic compositions.

2. The Related Art

Cosmetic products are often introduced to the consumer through promotional single or unit dose packages. Sealed capsules are one type of vehicle for delivering unit doses. Illustrative of this technology is U.S. Pat. No. 5,063,057 (Spellman et al) describing a gelatin capsule containing a cosmetic composition. The capsule is in the form of a Saturn-like shape defined by a round body with hollow chamber, a circumferential projecting ring encompassing the round body, a tab and a neck section connecting the tab with the round body. The cosmetic composition is released by twisting the neck to puncture the gelatin wall. A major problem with this package is that it does not allow for resealability; this is a single use item.

A multi-dosage containing Saturn-shaped container is known from U.S. Pat. No. 5,064,082 (Lombardi et. al.). This container has been used in commerce as a receptacle for the capsules described in U.S. Pat. No. 5,063,057. Not only is cost a problem in miniaturizing the container for small dosage delivery, but there also is a problem with adequate resealability for a liquid fill not confined by capsules.

Accordingly, it is an object of the present invention to provide a cosmetic product for small dosage delivery of a liquid cosmetic in a resealable package.

Another object of the present invention is to provide a cosmetic product in a resealable container that can be manufactured at relatively low cost.

A still further object of the present invention is to provide a cosmetic product in a resealable container that is completely accessible to a consumer's fingers so as to allow scooping of cosmetic product therefrom.

These and other objects of the present invention will become more apparent upon reference to the following detailed description and drawings illustrating a preferred embodiment thereof.

SUMMARY OF THE INVENTION

A cosmetic product is provided that includes:

a cosmetic composition pharmaceutically acceptable for application to a human body; and a container for enclosing the cosmetic composition including:

(i) a first section defined by a hemispheroidal chamber having an open mouth with a circumferential edge therearound, a flange projecting outwardly from and at least partially encompassing the circumferential edge, and a sealing web completely covering the mouth as well as at least a portion of the flange; and (ii) a second section defined by a hemispheroidal chamber having an open mouth with a circumferential edge therearound, a flange projecting outwardly from and at least partially encompassing the circumferential edge, a lip at least partially encompassing a peripheral edge of the flange, and at least one clamping device formed on the lip for releasably engaging the first section flange thereby releasably joining first and second sections to one another.

Advantageously, each of the hemispheroidal chambers forms at least one-half of either a round or oblate shell. Preferably the first and second sections are symmetric with respect to a plain of symmetry bisecting the container.

Also of advantage is that the first chamber, and respective flange, are formed as a unitary item. The second chamber, respective flange, respective lip and clamping device may also be formed as a unitary component. A transparent plastic may be utilized to form the second section.

The web may be a metallized foil. Aluminum foil is useful for this purpose. The web is adhesively sealed to the first flange. A variety of adhesives may be employed.

The lip is L-shaped and defined by an orthogonal first and second arm, the first arm being attached to the flange circumferentially therealong and projecting upwardly perpendicular thereto. The clamping device can be formed on the first arm as a ridge projecting inwardly toward the hemispheroidal chamber. Advantageously, four separate ridges will be equidistantly spaced circumferentially along the first arm.

An opening mechanism is formed along the first flange for assisting and separating the web from the first flange thereby opening the chamber mouth. The first flange is symmetrically round encompassing the hemispheroidal chamber except for a straight-cut segment serving as part of the opening mechanism.

Among suitable cosmetic compositions that may be dispensed through the container are those in lotion, or paste form. These products are intended for application to either hair or skin. The skin compositions may include agents providing sunscreen, tanning, antiwrinkling, antidandruff, antiacne, moisturizing and hair growth benefits.

BRIEF DESCRIPTION OF THE DRAWING

The accompanying drawing will more fully illustrate selected embodiments of the present invention wherein:

FIG. 1 is a side elevational view with partial cutaway of one embodiment of the container according to the present invention;

FIG. 2 is a bottom plan view of the first section of the container as seen in direction A shown in FIG. 1;

FIG. 3 is a top plan view of the first section of the container as seen in direction B shown in FIG. 1;

FIG. 4 is a side elevational view of the second section of the container as shown in FIG. 1;

FIG. 5 is a bottom plan view of the second section of the container as seen in direction A shown in FIG. 1; and FIG. 6 is an expanded partial side view of an L-shaped lip formed along an outer circumference of the second section.

DETAILED DESCRIPTION

FIG. 1 illustrates container 1 for holding a cosmetic composition 2. The container has a first section 4 and a second section 6.

The first section as shown in FIG. 2 includes a first hemispheroidal chamber 8 and first flange 10. FIG. 3 illustrates the open mouth 12 of the first hemispheroidal chamber 8. A circumferential edge 14 defines the outer boundary of open mouth 12. A sealing web or foil 16 covers the open mouth 12 and is adhesively sealed to flange 10.

FIG. 4 illustrates the second section 6 with its hemispheroidal chamber 18 and flange 20. FIG. 5 depicts the second section 6 component structures with the hemispheroidal chamber 18 formed with an open mouth 22 defined by circumferential edge 24 from which flange 20 projects outwardly. A lip 26 circumferentially encompasses a peripheral edge 27 of flange 20. A clamping device 28 is formed on lip 26. FIG. 6 illustrates the lip as consisting of a first arm 30 and a second arm 32. The clamping device is in the form of a ridge 34 that can releasably engage the first section flange 10 thereby releasably joining the first and second sections 4, 6 to one another.

The second hemispheroidal chamber 18, flange 20, lip 26 and clamping device 28 are advantageously formed as a unitary component. This may be accomplished through injection molding as a one-piece item. Similarly, the first hemispheroidal chamber 8 and respective flange 10 may also be formed as a unitary component. Sealing web 16 is best utilized in the form of an aluminum foil. This foil is adhesively sealed to flange 10.

Lip 26 is L-shaped and defined by the orthogonal arms 30 and 32. Arm 30 is attached to flange 20 and projects upwardly perpendicular thereto. The clamping device 28 is formed on the first arm as a ridge 34 projecting inwardly toward the hemispheroidal chamber 18. Most effective is a series of four equidistantly spaced ridges 34.

The opening mechanism 36 is formed along the flange 10. This mechanism assists in separating the web from the first flange thereby opening the chamber mouth. The first flange 10 is symmetrically round encompassing the hemispheroidal chamber 8 except for a straight cut segment 38 which defines the opening mechanism 36.

The first section 4 is advantageously composed of polypropylene vacuum formed to achieve a 30-gauge thickness. The second section may also be vacuum formed and is composed of either polyvinyl chloride (PVC) or polyethylene terephthalate (PET). Cosmetic composition sample sizes of around ⅛ ounce can be accommodated by the preferred embodiment size.

Lotion, cream and paste forms may be packaged within the chamber of the first section 4. These compositions may either be anhydrous, aqueous or in emulsion form, the latter encompassing both oil-in-water and water-in-oil emulsions.

Cosmetic compositions of the present invention generally will contain a vehicle or a carrier which is inert, usually an ingredient present in highest amounts, and functioning to deliver active or performance ingredients. The amount of vehicle may range from about 5 to about 99%, preferably from about 25 to about 80% by weight of the total composition.

Silicone polymers may be a useful component of the compositions. Especially preferred is polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under the trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

Surfactants, which are also sometimes designated as emulsifiers, may be incorporated into the cosmetic compositions of the present invention. Surfactants can comprise anywhere from about 0.5 to about 30%, preferably from about 1 to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulfonate, mono and dialkyl acid phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5 to about 50%, preferably between about 5 and 30% by weight of the total composition. Emollients may be classified under such general chemical categories as esters, fatty acids and alcohols, polyols and hydrocarbons.

Esters may be mono- or diesters. Acceptable examples of fatty diesters include dibutyl adipate, diethyl sebacate, diisopropyl dimerate, and dioctyl succinate. Acceptable branched chain fatty esters include 2-ethylhexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl erucate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin antiwrinkling agents, antidandruff agents, antiacne agents and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Antiwrinkling agents are best exemplified by the 2-hydroxyalkanoic acids, prostaglandins, retinoic acids, ceramides and their derivatives. These agents may be present anywhere from about 0.0000to about 5%, preferably from about 0.0001 to about 1%, optimally between about 0.01 and 0.2% by weight of the total composition. Most preferred of the active compounds mentioned above is 2-hydroxyoctanoic acid, retinol and pigskin or bovine-brain lipid ceramides. Further identification of ceramide structures may be found in U.S. Pat. No. 4,950,688 (Bowser et al), herein incorporated by reference.

Vitamins may also be included in the compositions of the present invention. Especially preferred is vitamin A palmitate (retinyl palmitate) and vitamin E linoleate (tocopheryl linoleate). Other esters of vitamins A and E may also be utilized.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic compositions of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001 up to 20% by weight of the composition.

The following examples will more fully illustrate selected embodiments of this invention. All parts, percentages and proportions referred to herein and in the appended claims are by weight unless otherwise indicated.

EXAMPLE 1

A skin care treatment according to the invention may be of the following composition:

| SKIN CARE TREATMENT | |
|---|---|
| Ingredient | Wt. % |
| Silicone Gum SE-30 | 10.00 |
| Silicone Fluid 345 | 20.00 |
| Silicone Fluid 344 | 58.49 |
| Squalene | 10.00 |
| Ceramides | 0.01 |
| Vitamin A Palmitate | 0.50 |
| Vitamin E Linoleate | 0.50 |
| Herbal Oil | 0.50 |

EXAMPLE 2

A suntan lotion according to the invention may be of the following composition:

| SUNTAN LOTION | |
|---|---|
| Ingredient | Wt. % |
| Water | 86.00 |
| Acetulan (cetyl acetate and acetylated lanolin alcohol) | 4.00 |
| Propylene glycol | 3.00 |
| Stearic acid | 2.00 |
| Dow Corning 556 Fluid (phenyl dimethicone) | 1.00 |
| Veegum (modified magnesium aluminum silicate) | 1.00 |
| Cetyl alcohol | 0.50 |
| Triethanolamine | 0.50 |
| Octyl methoxycinnamate | 1.00 |
| Oxybenzone | 1.00 |
| Preservatives | qs |

EXAMPLE 3

An acne lotion according to the invention may be of the following composition;

| ACNE LOTION | |
|---|---|
| Ingredient | Wt. % |
| Deionized water | 82.60 |
| Glycerin | 3.00 |
| Glyceryl monstearate | 3.00 |
| Smectite clay | 2.00 |
| Stearyl alcohol | 1.00 |
| Isocetyl stearate | 1.00 |
| Preservatives | 0.40 |
| Benzoyl peroxide | 7.00 |

EXAMPLE 4

A skin wrinkle smoother according to the invention may be of the following composition:

| SKIN WRINKLE SMOOTHER | |
|---|---|
| Ingredients | Wt. % |
| Water | 82.50 |
| Flexan 130 (sodium polystyrene sulfonate) | 12.00 |
| Collasol soluble collagen | 3.00 |
| Modified magnesium aluminum silicate | 1.50 |
| Cellulose gum CMC-7LF | 1.00 |

EXAMPLE 5

An antidandruff shampoo according to the invention may be of the following composition:

| ANTIDANDRUFF SHAMPOO | |
|---|---|
| Ingredient | Wt. % |
| Water | 58.55 |
| TEA lauryl sulfate (40%) | 25.00 |
| Hamposyl L-30 fatty acid sarcosinate | 10.00 |
| Zinc pyrithione (48%) | 4.20 |
| Hydroxypropyl methylcellulose | 1.25 |
| Modified magnesium aluminum silicate | 1.00 |

EXAMPLE 6

A hair growth stimulant according to the invention may be of the following composition:

| HAIR GROWTH STIMULANT | |
|---|---|
| Ingredient | Wt. % |
| Water | 60.15 |
| Sodium lauryl ether sulfate | 28.00 |
| Sodium sulfate | 10.00 |
| Lanolin alcohol | 1.00 |
| Polyoxyethylene 20 sorbitan | 0.50 |
| Minoxidil | 0.25 |
| Methylparaben | 0.10 |

The foregoing description and examples illustrate selected embodiments of the present invention and in light thereof variations and modifications will be suggested to one skilled in the art, all of which are within the spirit and purview of this invention.

What is claimed is:

1. A cosmetic product comprising:
   a cosmetic composition pharmaceutically acceptable for application to a human body; and
   a container for enclosing the cosmetic composition comprising:
   (i) a first section defined by a hemispheroidal chamber having an open mouth with a circumferential edge therearound, a flange projecting outwardly from and at least partially encompassing the circumferential edge, and a sealing web completely covering the mouth as well as at least a portion of the flange; and
   (ii) a second section defined by a hemispheroidal chamber having an open mouth with a circumferential edge therearound, a flange projecting outwardly from and at least partially encompassing the circumferential edge, a lip at least partially encompassing a peripheral edge of the flange, and at least one clamping means formed on the lip for releasably engaging the first section flange thereby releasably joining first and second sections to one another.

2. A cosmetic product according to claim 1 wherein each hemispheroidal chamber forms at least one-half of a symmetrically round shell.

3. A cosmetic product according to claim 1 wherein each hemispheroidal chamber forms at least one-half of an oblate shell.

4. A cosmetic product according to claim 1 wherein the first and second sections are symmetrical with respect to a plain bisecting the respective flanges.

5. A cosmetic product according to claim 1 wherein the first hemispheroidal chamber and respective flange are formed as a unitary component.

6. A cosmetic product according to claim 1 wherein the second hemispheroidal chamber, respective flange, respective lip and clamping means are formed as a unitary component.

7. A cosmetic product according to claim 1 wherein the second section is formed of a transparent plastic.

8. A cosmetic product according to claim 1 wherein the web is a metallized foil.

9. A cosmetic product according to claim 8 wherein the metallized foil is formed of aluminum.

10. A cosmetic product according to claim 1 wherein the web is adhesively sealed to the flange of the first section.

11. A cosmetic product according to claim 1 wherein the lip is L-shaped and defined by an orthogonal first and second arm, the first arm being attached to the flange and projecting upwardly perpendicular thereto.

12. A cosmetic product according to claim 11 wherein the clamping means is formed on the first arm as a ridge projecting inwardly toward the second hemispheroidal chamber.

13. A cosmetic product according to claim 12 wherein there are four equidistantly spaced ridges.

14. A cosmetic product according to claim 1 further comprising an opening means formed along the first flange for assisting in separating the web from the first flange to thereby open the first hemispheroidal chamber mouth.

15. A cosmetic product according to claim 14 where the first flange is symmetrically round encompassing the first hemispheroidal chamber except for a straight-cut segment serving as part of the opening means.

16. A cosmetic container for enclosing a cosmetic composition comprising:
   (i) a first section defined by a hemispheroidal chamber having an open mouth with a circumferential edge therearound, a flange projecting outwardly from and at least partially encompassing the circumferential edge, and a sealing web completely covering the mouth as well as at least a portion of the flange; and
   (ii) a second section defined by a hemispheroidal chamber having an open mouth with a circumferential edge therearound, a flange projecting outwardly from and at least partially encompassing the circumferential edge, a lip at least partially encompassing a peripheral edge of the flange, and at least one clamping means formed on the lip for releasably engaging the first section flange thereby releasably joining first and second sections to one another.

* * * * *